United States Patent [19]

Ozaki

[11] 4,334,534
[45] Jun. 15, 1982

[54] EMERGENCY AIRWAY MANAGEMENT DEVICE

[75] Inventor: George T. Ozaki, San Diego, Calif.

[73] Assignee: The Regents of the University of California, Berkeley, Calif.

[21] Appl. No.: 188,180

[22] Filed: Sep. 18, 1980

[51] Int. Cl.³ .......................................... A61M 25/00
[52] U.S. Cl. ............................................. 128/207.15
[58] Field of Search .................... 128/207.15, 207.14, 128/349 B, 349 R, 349 BV

[56] References Cited

U.S. PATENT DOCUMENTS

| | | | |
|---|---|---|---|
| 3,683,908 | 4/1972 | Don Michael et al. | 128/207.15 |
| 3,905,361 | 9/1975 | Hewson et al. | 128/349 B |
| 4,018,231 | 4/1977 | Wallace | 128/207.15 |
| 4,150,676 | 4/1979 | Jackson | 128/207.15 |
| 4,231,365 | 11/1980 | Scarberry | 128/207.15 |
| 4,235,239 | 11/1980 | Elam | 128/207.15 |

*Primary Examiner*—Henry J. Recla
*Attorney, Agent, or Firm*—Warren T. Jessup

[57] ABSTRACT

An emergency airway tube for use in resuscitation of non-breathing patients by inserting the tube through the mouth until it randomly lodges either in the trachea or the esophagus. Only one insertion is needed. The tube is designed to ventilate the lungs regardless of which passageway it is lodged in. The tube has three tubes—the outer tube, an inner tube, which runs along and within the bore of the outer tube, and an air passageway for inflating an inflatable cuff located at the distal end of the outer tube which enters the trachea or esophagus. The end of the inner tube has a pneumatic seal for forming an airtight fit within and adjacent the distal end of the outer tube. The outer tube has a cluster of side air ports in its wall located generally midway between the ends of the tube. If the tip of the tube engages the trachea on insertion, the cuff is inflated and the inner tube will be the air passageway to ventilate the patient. If the tip of the tube engages the esophagus, the cuff will seal off the stomach. The outer tube will be the air passageway to ventilate the lungs by way of the side air ports in the outer tube's wall. A face mask is placed over the face of the patient to stop air leakage while the patient is being ventilated via the air ports.

1 Claim, 10 Drawing Figures

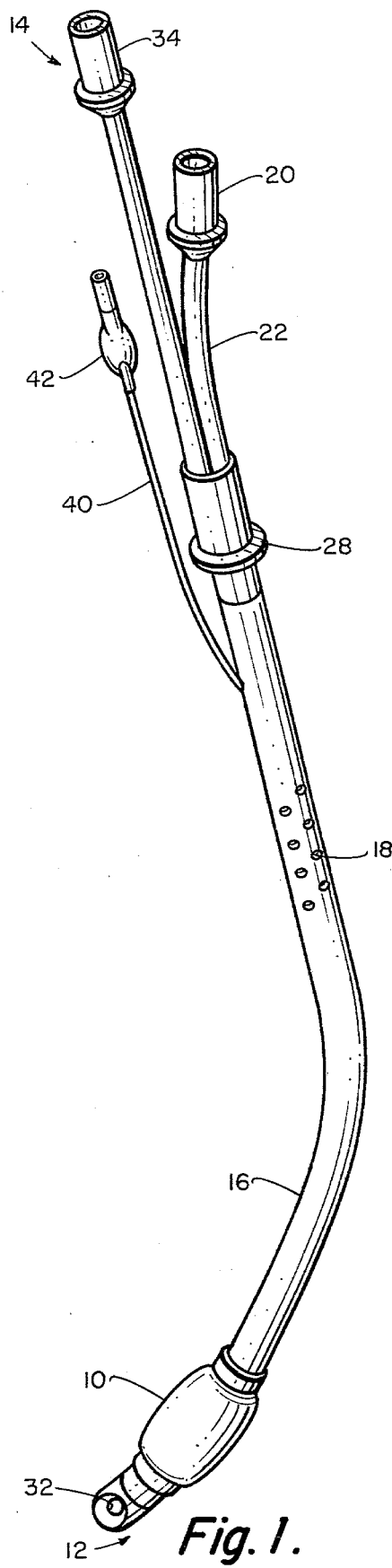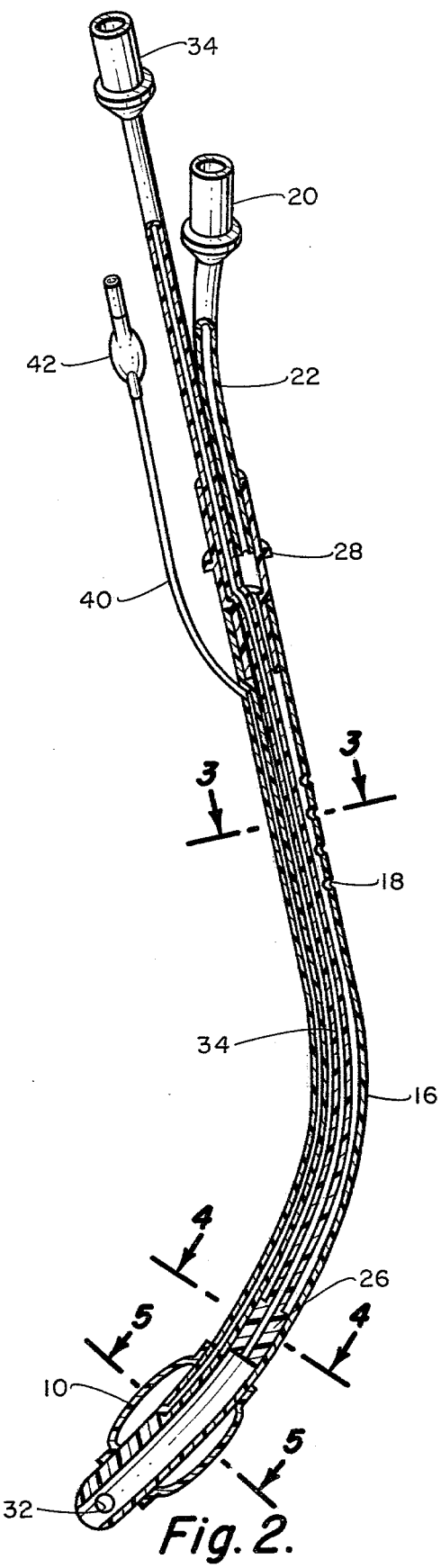

EMERGENCY AIRWAY MANAGEMENT DEVICE

BACKGROUND OF THE INVENTION

This invention relates to emergency resuscitation of a patient who has been asphyxiated, drowned, or suffered a heart attack or electric shock, or the like. Common to all these patients is the fact that they have stopped breathing. It is medically necessary under these conditions to ventilate the lungs to provide oxygen to the body to prevent irreversible damage to the brain and other vital organs and cells.

The most effective instrument for this purpose is the endotracheal tube, which is a tube placed directly in the trachea or windpipe. The drawback to this device is that it must be inserted by an anesthesiologist, with hospital facilities, not normally available when the above-elaborated emergencies occur. The need has been apparent and various devices have been designed which will be relatively simple to insert and operate.

Esophageal airway devices presently being marketed do not replace endotracheal intubation, which provides optimal control of the airway. The primary advantage to esophageal intubation is that these devices can be passed blindly into the esophagus without need for laryngoscopic visualization of the larnyx and associated structures. Therefore, it can be used by paramedical and medical personnel who have much less training than is required to achieve competence in the use of an endotracheal tube.

Common to all the esophageal devices is the necessity of inserting the tube into the esophagus before it can function to ventilate the patient. However, it is fairly common for even a medically trained technician to mistakenly insert these devices into the trachea. Valuable time can be lost in the trial and error method of inserting these tubes into the proper passage.

SUMMARY OF THE INVENTION

Accordingly, it is an object of the present invention to provide an improved emergency airway management device, which contains the features of an endotracheal tube and an esophageal obturator into one device, which substantially overcomes the above-mentioned drawbacks in the prior art.

In a life-threatening situation, where a patient stops breathing because of a heart attack, electric shock, drowning, or the like, it is absolutely necessary to oxygenate the victim's lungs to prevent irreversible physiological brain or cellular damage. The present invention saves precious time when resuscitating a patient. The device only needs to be blindly inserted once. Thereafter the attending personnel can quickly determine which lumen the tube has engaged, i.e., the trachea or esophagus. Thereafter the attending personnel can connect the proper tubing for correctly ventilating the patient. The present invention ends the trial and error method presently necessary with the esophageal obturator devices, where the attending personnel must waste precious seconds or minutes in trying to engage the tube with the esophagus.

In accordance with the present invention, an emergency airway management device is inserted into the mouth of a patient for introducing gas into the lungs by way of the airway device, through the trachea and into the lungs. The device has an outer tube which contains airports in its outer wall generally midway between its ends. The purpose of these airports is to provide a passage for air when the device is used as an esophageal obturator tube. Air is injected into the bore of the outer tube. The air exits through the airports and into the pharynx area of the patient and into the lungs. An inflatable cuff is attached towards the distal end of the outer tube. It is fixedly attached to and encircles the outer circumference of the outer tube, adjacent the outer tube's distal end. An airline runs from the cuff along or within the wall of the outer tube and emerges at the proximal end of the outer tube and terminates at the airline's proximal end with a pilot balloon.

The cuff is formed of a relatively soft and pliable material capable of expanding upon the introduction of air into the cuff. Pressurized air is introduced through the connection with the pilot balloon and flows through the airline to the inflatable cuff. After the airway device has been correctly positioned within the trachea or esophagus of the patient, the cuff is inflated to a snug fit to seal the device to prevent leakage of air and secretions between the cuff and the walls of the trachea or esophagus. The pilot balloon is a pressure indicator to indicate to the attending personnel the amount of inflation in the cuff.

Running along and within the bore of the outer tube is an inner tube. The inner tube could be oval shaped and the outer tube could be oval shaped, if desired. The cross-configuration of either inner or outer tube can be any generally circular shape. The concentric shape of the outer tube and inner tube and airtight seal are disclosed as the most economical configuration for the manufacture of the airway device.

The inner tube terminates adjacent the distal end of the outer tube with an annular seal, which forms an airtight seal to prevent air leakage whenever the outer tube is pressurized with air. If the tip of the outer tube lodges in the esophagus, the inner tube can function as a conduit for placing a stomach drain tube into the stomach. A small tube can be threaded through the inner tube, past the distal end of the outer tube and passed into the stomach. Standard procedures can be employed using the stomach drain tube to evacuate the contents of the stomach, if necessary.

These, as well as other objects of the present invention, will become apparent from the following detailed description when viewed in conjunction with the accompanying drawings, wherein like numbers identify like parts throughout.

MODE OF OPERATION

The airway device is designed to function when placed within either the trachea or the esophagus. The patient is placed in a prone position. The airway device is inserted through the mouth of the patient, past his tongue and inserted to the length of the tube. After placement of the tube, the cuff is inflated to a snug fit. The tip of the tube has lodged either in the trachea or the esophagus and it can, and must, be determined in which passage it has lodged.

The endotracheal connection is hooked up to a mechanical ventilator and pressurized air is injected through inner tube and exits out of the distal end of the outer tube and into the patient. If this causes chest expansion of the patient, then the distal tip of the tube is in the trachea. In effect, the tube is functioning as an endotracheal tube. The patient can be ventilated by way of the mechanical connections. Gastric distention can be relieved by passing a naso-gastric tube into the stomach.

If the chest of the patient does not expand upon injection of pressurized air through the inner tube, the tip of the tube must thereby be lodged in the esophagus. The mechanical ventilator is hooked up to the esophageal airway connector which injects pressurized air into the bore of the outer tube. The air passes through the air ports, into the trachea and then into the lungs. A standard face mask is used to seal the oropharynx from outboard leaks. Gastric distention can be relieved by passing a gastric tube via the inner tube and into the stomach.

The airway device gives the standard esophageal airway devices more flexibility for the establishment of an artificial airway in an emergency situation.

BRIEF DESCRIPTION OF THE DRAWINGS

FIG. 1 is a perspective view illustration of the emergency airway management device showing the cuff at the distal end, and the mechanical connectors and pilot balloon at the proximal end.

FIG. 2 is a longitudinal cross-sectional view of the emergency airway device of FIG. 1.

DETAILED DESCRIPTION OF THE PREFERRED EMBODIMENT

Figure 3:
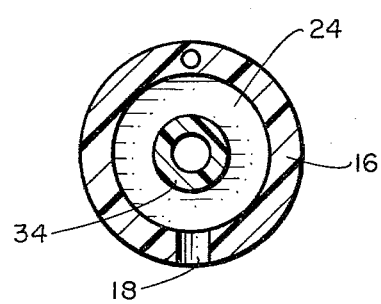
FIG. 3 is a transverse cross-sectional view through the medial arch of the FIG. 1 device, the view being taken along the line 3—3 of FIG. 2.

Referring now to FIG. 1, the emergency airway device consists generally of an elongated curved tubular configuration having a cuff 10 or balloon at its distal end 12 and three connectors at its proximal end 14. It includes an outer tube 16, which is hollow throughout its length. The outer tube 16 is normally twelve inches in length and 8 mm in diameter, which is of sufficient dimension to accommodate the average adult. The outer tube 16 could be fabricated from rubber, or plastic, such as nylon, polyethylene, polyurethane, polyvinyl chloride, silicone, Silastic, or the like. Silastic is a trademark for a silicone material which is inert and compatible with biological tissues. The trademark owner is Dow-Corning.

The outer tube can be formed from a rigid or flexible material with the overall configuration being of a generally curved shape to facilitate insertion through the mouth and over the tongue of the patient. The curve would be compatible with the general arch-shaped passage which the human body provides between the mouth and the esophagus or trachea. The curved shape is unnecessary when the device is formed from a flexible material.

The outer tube 16 has several side air ports 18 clustered towards, and around, the medial area of the outer tube 16. The purpose of these air ports 18 is to provide openings for air ventilation when the esophageal connector 20 is attached to a mechanical ventilator, airbag, or the like (not shown). This connector 20 would be used whenever the airway device has lodged in the patient's esophagus. The air flows from the mechanical ventilator, through the esophageal tube 22 and into the bore 24 of the outer tube 16. The annular seal 26 and the sleeve 28 on the proximal end 14 of the outer bore 16 prevent any air leakage. Therefore, the air can only flow out of the air ports 18. Furthermore, after the air escapes from the air ports 18 of the outer bore 16, it is prevented by the inflated cuff 10 from leaking past it and into the stomach via the esophagus. A face mask 30 is utilized to seal against any outboard leaks. The pressurized air enters the lungs because it has no other escape route.

In one embodiment, the distal end 12 of the outer tube 16 is angularly cut with a hole 32 opposite the side of the angle. Running along and within the bore 24 of the outer tube 16 is the inner tube 34 which terminates at the distal end 12 with an annular seal 26. The inner tube 34 extends about twelve inches beyond the end of the outer tube 16 and terminates with an endotracheal connector 34, which can be a standard 15 mm endotracheal connector.

Figure 6:
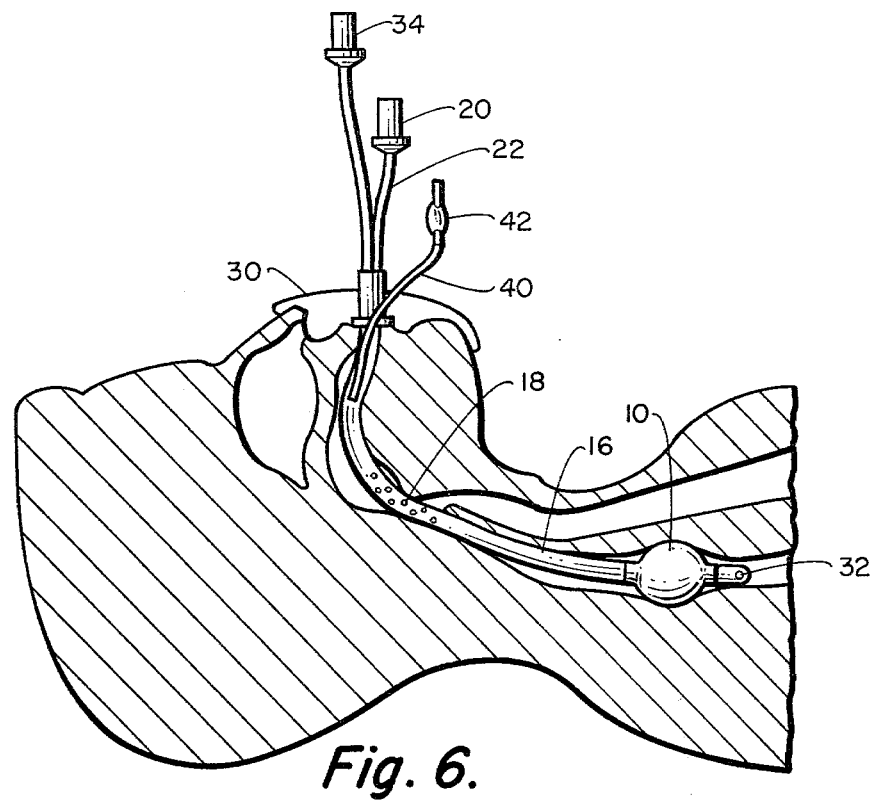
FIG. 6 is a medial sectional view illustrating the operation of the emergency airway device when lodged in the esophagus.

A sleeve 28 positions the inner tube 34 within the bore 24 of the outer tube 16. The inner tube 34 can be comprised of the same type of material as previously stated for the outer tube 16. The overall diameter of the inner tube 34 should be small enough compared to the bore 24 so as not to restrict air flow when the emergency airway device has randomly lodged in the esophagus 13, as illustrated in FIG. 6, and the outer tube 16 is being used to ventilate the patient.

As illustrated in the transverse cross-sectional view of FIGS. 3, 4, 5 and 10, the preferred embodiments of the outer tube 16 and the inner tube 34 are circular throughout in their cross-sections. Using a larger circular tube and a smaller circular tube placed within it appears to be the most economical way to manufacture the device. However, the utility of the device is unimpaired if the cross-section of either tube is of a noncircular configuration.

Figure 4:
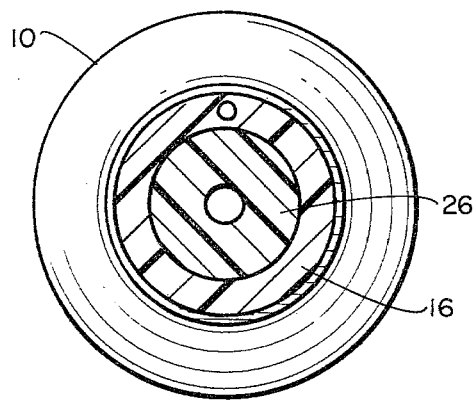
FIG. 4 is a transverse cross-sectional line through the sealing means of the FIG. 1 device, the view taken along the line 4—4 of FIG. 2.
Figure 5:
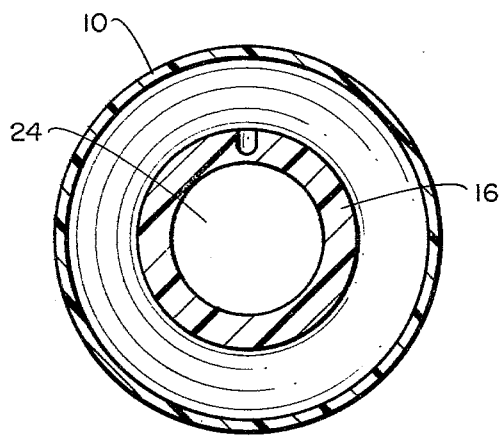
FIG. 5 is a transverse cross-sectional line through the main cuff of the FIG. 1 device, the view taken along line 5—5 of FIG. 2.
Figure 10:
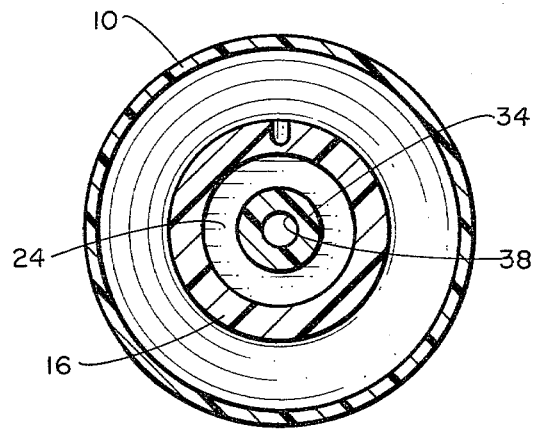
FIG. 10 is a transversal sectional view of the FIG. 8 device taken along the line 10—10 of FIG. 9 illustrating the main cuff.
Figure 8:
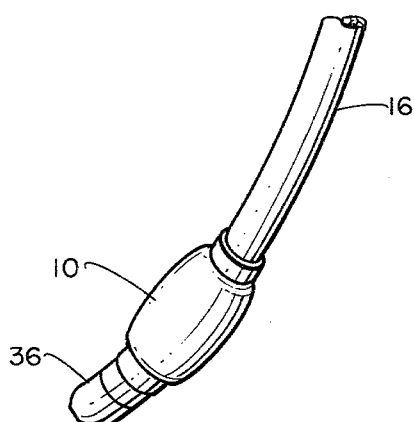
FIG. 8 is a partial perspective view illustrating a second embodiment of the distal tip and sealing means of the FIG. 1 device.
Figure 9:
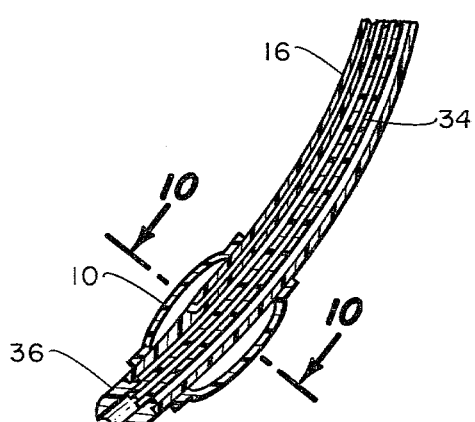
FIG. 9 is a partial longitudinal sectional view of the FIG. 8 device illustrating the second embodiment sealing means.

FIG. 4 illustrates the transverse cross-sectional view of the interior annular seal 26. Seal 26 discloses the preferred embodiment of the seal, as illustrated in FIG. 2. FIGS. 8 and 9 disclose the second embodiment of the device in which the annular seal is a round-headed seal 36 inserted in the tip of the distal end 12 of the outer tube 16. It could be a tight slip-in type of fit to form the airtight seal. The seal 36 has a bore 38 in the center of it. The distal end of the inner tube 34 communicates with the bore 38 to also form an airtight seal. In this fashion, injected air into the bore 38 of the outer tube 16 cannot leak past this seal. It is important this does not occur because when the device is used as an esophageal obturator tube, air leakage would result in partial distension of the stomach and also reduce the efficiency of the device by impairing the amount of air reaching the lungs.

The interior seal 26 is preferably an annular seal with an outside diameter equal to the diameter of the bore 24 of the outer tube 16. The bore of the annular seal is preferably the same diameter as the outer diameter of the inner tube 34. The purpose of the seal 26 having this diameter is to provide a snug fit as illustrated in FIG. 4. When in place, the airtight seal 26 prevents any air leakage past it when air is introduced by way of the esophageal airway connector 20. The seal 26 or 36 could be held in place by a compression fit, suitable adhesive, or, if desired, could be molded as part of the outer tube.

The esophageal airway connection 22 communicates with the proximal end of the outer tube 16 by being sealed with an airtight fit in conjunction with the sleeve 28. The other end of the connection 22 terminates with a standard 15 mm diameter connector for connection to a mechanical ventilator or airbag to ventilate the patient after insertion of the emergency airway device.

As illustrated in FIG. 1 and FIG. 8, the outer tube 16 has an inflatable cuff 10 which forms an effective seal between the walls of the trachea or esophagus, depending upon which passage the device has lodged in, and the outer tube 16. In the preferred embodiment of the invention, the exterior sealing means is an air inflatable cuff 3 which is connected to air line 40, emerging towards the proximal end of the outer tube 16 and terminates with a pilot balloon and connector 42. The pilot balloon 42 serves as a visual indicator of the amount of pressure in the cuff 10. The air line 40 could be a bore within the wall of the outer tube 16, or it could be an air line attached to the inside or outside wall of the outer tube 16. The cuff 10 is designed for providing the snug fit required for this type of device. It prevents leakage of air and of secretions around the tube 16 and aspiration of vomitus and oropharyngeal secretions when the emergency airway device is in place.

Figure 7:
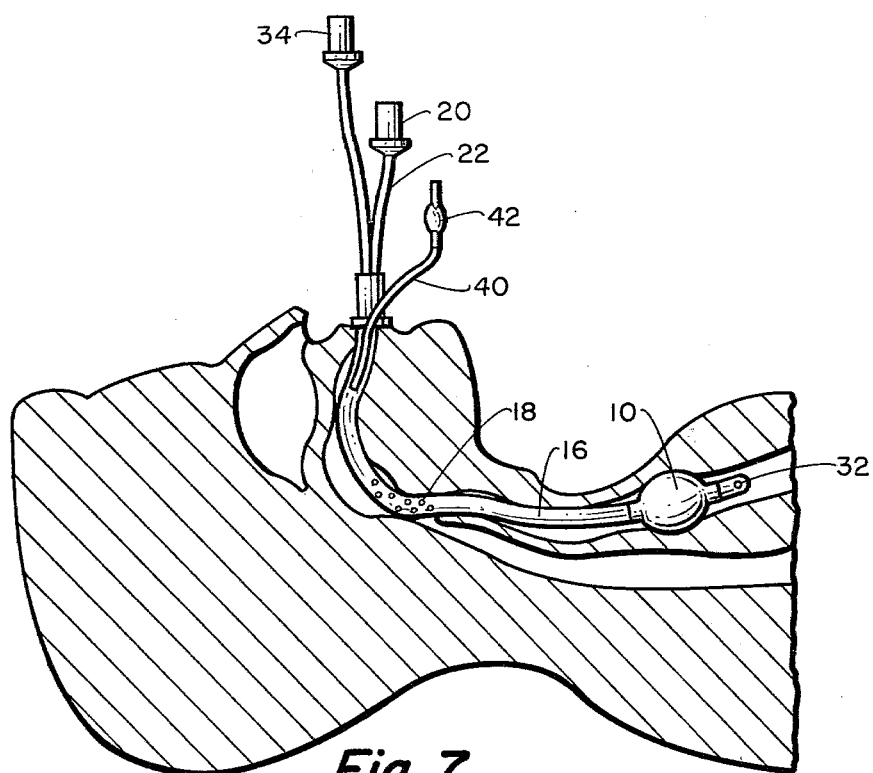
FIG. 7 is a medial sectional view illustrating the operation of the emergency airway device when lodged in the trachea.

FIGS. 6 and 7 illustrate the position of the emergency airway device while in actual use. In these illustrations the outer tube 16 is fabricated from a flexible material to allow a bending of the device while being inserted. The face mask 30 could be any type of standard surgical-type mask which is used to prevent outbound air leakage when the device is inserted in the esophagus as illustrated in FIG. 6.

The face mask is not necessary when the device has lodged in the trachea as illustrated by FIG. 7, because the inflatable cuff 10 prevents air leakage out of the trachea. The pressurized air is inserted through the endotracheal connector 34 which is attached to the inner tube 34. The air exits at the distal end 12 of the outer tube 16, which is below the cuff 10. The mechanical ventilator can inject air into the patient in a variety of ways, such as pressure cycled, volume cycled. The ventilator should be used and adjusted according to the manufacturer's specifications.

The foregoing detailed description of the present invention is given for clearness of understanding only, and no unnecessary limitations should be understood therefrom. Accordingly, the invention is broadly construed and limited only by the scope and spirit of the claims appended hereto.

What is claimed is:

1. A flexible emergency airway device for insertion through the mouth and randomly lodging either in the trachea or esophagus for resuscitating a patient, which comprises:

an outer tube having a distal end and a proximal end and having at least one air port in the wall of said outer tube located intermediate the distal and proximal ends of said outer tube, said distal end of said outer tube being angularly cut and having a side port in the wall of said outer tube opposite from said angular cut;

inner tube means for providing an airway through the mouth of a patient, placed longitudinally along and within the bore of said outer tube and terminating adjacent the distal end of said outer tube;

interior sealing means for forming an airtight seal between the exterior wall of said inner tube means and interior wall of said outer tube and placed between said air port and the distal end of said inner tube means;

exterior sealing means for forming an effective seal with the walls of the trachea or esophagus depending upon which passage said outer tube is lodged in, and attached adjacent said distal end and encircling said outer tube;

a pilot balloon connected to said exterior sealing means by a passageway for indicating the amount of pressure in said exterior sealing means, and providing a means for inflating and deflating said exterior sealing means.